US010525254B2

(12) United States Patent
Miller (10) Patent No.: US 10,525,254 B2
(45) Date of Patent: Jan. 7, 2020

(54) CUTANEOUS ELECTRODE

(71) Applicant: NeuroSigma, Inc., Los Angeles, CA (US)

(72) Inventor: Patrick Miller, Los Angeles, CA (US)

(73) Assignee: NEUROSIGMA, INC., Los Angeles, CA (US)

(*) Notice: Subject to any disclaimer, the term of this patent is extended or adjusted under 35 U.S.C. 154(b) by 0 days.

(21) Appl. No.: 15/594,455

(22) Filed: May 12, 2017

(65) Prior Publication Data

US 2017/0246447 A1    Aug. 31, 2017

Related U.S. Application Data

(60) Division of application No. 14/671,969, filed on Mar. 27, 2015, now Pat. No. 9,675,794, which is a continuation of application No. PCT/US2013/062749, filed on Sep. 30, 2013.

(60) Provisional application No. 61/707,859, filed on Sep. 28, 2012.

(51) Int. Cl.
*A61N 1/04* (2006.01)
*A61N 1/36* (2006.01)

(52) U.S. Cl.
CPC ......... *A61N 1/0492* (2013.01); *A61N 1/0456* (2013.01); *A61N 1/36025* (2013.01)

(58) Field of Classification Search
CPC .................... A61N 1/36025; A61N 1/0456
See application file for complete search history.

(56) References Cited

U.S. PATENT DOCUMENTS

| | | | |
|---|---|---|---|
| 2003/0069627 | A1 | 4/2003 | Giuntoli et al. |
| 2007/0060975 | A1 | 3/2007 | Mannheimer et al. |
| 2008/0275327 | A1 | 11/2008 | Faarbaek et al. |
| 2009/0210028 | A1* | 8/2009 | Rigaux ............. A61N 1/0456 607/46 |
| 2010/0198044 | A1 | 8/2010 | Gehman et al. |
| 2010/0228113 | A1* | 9/2010 | Solosko ............. A61B 5/0416 600/382 |

* cited by examiner

*Primary Examiner* — Christopher Koharski
*Assistant Examiner* — Philip C Edwards
(74) *Attorney, Agent, or Firm* — Haynes and Boone, LLP (57) ABSTRACT

A windowed electrode assembly includes a foam layer having windows. Each window receives a corresponding gel pad that is sized such that it is contained by the window's sidewalls. The windowed electrode assembly includes a foam backing layer that forms a back wall for the windows such that each gel pad is encased by the window's sidewalls and back wall.

20 Claims, 5 Drawing Sheets

CUTANEOUS ELECTRODE

CROSS-REFERENCE TO RELATED APPLICATIONS

This application is a divisional of U.S. patent application Ser. No. 14/671,969 filed Mar. 27, 2015 and entitled "CUTANEOUS ELECTRODE," which is a continuation of International Patent Application No. PCT/US2013/062749 filed Sep. 30, 2013 and entitled "CUTANEOUS ELECTRODE," which are hereby incorporated by reference in their entirety.

International Patent Application No. PCT/US2013/062749 claims the benefit of U.S. Provisional Patent Application No. 61/707,859 filed Sep. 28, 2012, which is hereby incorporated by reference in its entirety.

TECHNICAL FIELD

The present invention relates generally to electrodes for medical therapy, and more specifically to a cutaneous electrode adapted for cutaneous stimulation of the ophthalmic nerves.

BACKGROUND

Neurological disorders such as seizure disorders are usually treated with medication. However, there are patients who are not helped by medication—they may not be able to tolerate the side effects or the medication itself is not efficacious for their particular disorder. This is a significant problem in that seizure disorders can be life threatening. Moreover, the quality of life for victims of severe epilepsy can be severely impacted. Neuropsychiatric disorders such as depression and ADHD are also typically treated with medications that have deleterious side effects and lack of efficacy. To offer patients relief that medication alone cannot deliver, various neurostimulation methods have been developed. For example, vagus nerve stimulation (VGS) has been shown to be therapeutically useful. Similarly, deep brain stimulation (DBS) and responsive neurostimulation (RNS) approaches are known to have efficacy. But these neurostimulation techniques are invasive as they require surgical implantation of electrodes. Thus, these techniques are relatively expensive and involve the dangers associated with the surgical implantation of the electrodes.

To provide neurostimulation without the invasive dangers of prior art techniques, an alternative neurostimulation therapy has been developed that involves trigeminal nerve stimulation (TNS). For example, a cutaneous embodiment of TNS involves the transcutaneous stimulation of the supraorbital nerves and/or the supratrochlear nerves in the forehead. Like other cranial nerves, the supraorbital and supratrochlear nerves arise through foramina in the skull. The supraorbital nerve arises from the supraorbital foramen above the orbit. Since one has two eyes, there are thus two supraorbital nerves that ascend vertically toward the scalp from their respective foramen. The supratrochlear nerve is medial with regard to the supraorbital. But it also then ascends vertically towards the hairline. There are thus two supratrochlear nerves, each arising from its respective orbit. A supraorbital nerve and supratrochlear nerve thus associates with each orbit. The forehead is thus an ideal location to stimulate the trigeminal nerve in that the supraorbital nerve and supratrochlear nerve associated with each orbit are located medially on the forehead. The skin and fascia over the forehead is relatively thin such that the supratrochlear and supraorbital nerves are readily stimulated transcutaneously.

One approach to stimulate the supratrochlear and supraorbital nerves requires a clinician to palpate for the supraorbital notch or foramen so that a suitable electrode can be applied adjacent the notch. The electrode would be sized so that it would cover not only the trunk of the supraorbital as it arises from its foramen but also the trunk of the corresponding supratrochlear nerve. To provide bilateral stimulation, the clinician would also palpate for the remaining supraorbital notch and apply another electrode accordingly. Although such an approach provides advantageous neurostimulation for treatment of disorders without invasive implantations or deleterious pharmaceutical side effects, the treatment is burdened by the need for expert application of the electrodes. For example, if a lay person applies the electrodes in this fashion and locates the electrodes too laterally on the forehead, the resulting bilateral current excited between the two electrodes may penetrate to the brain. Thus, the application of electrodes in this fashion required medical expertise, which greatly increases costs as the patient must visit a medical facility daily for chronic treatments.

Figure 1:
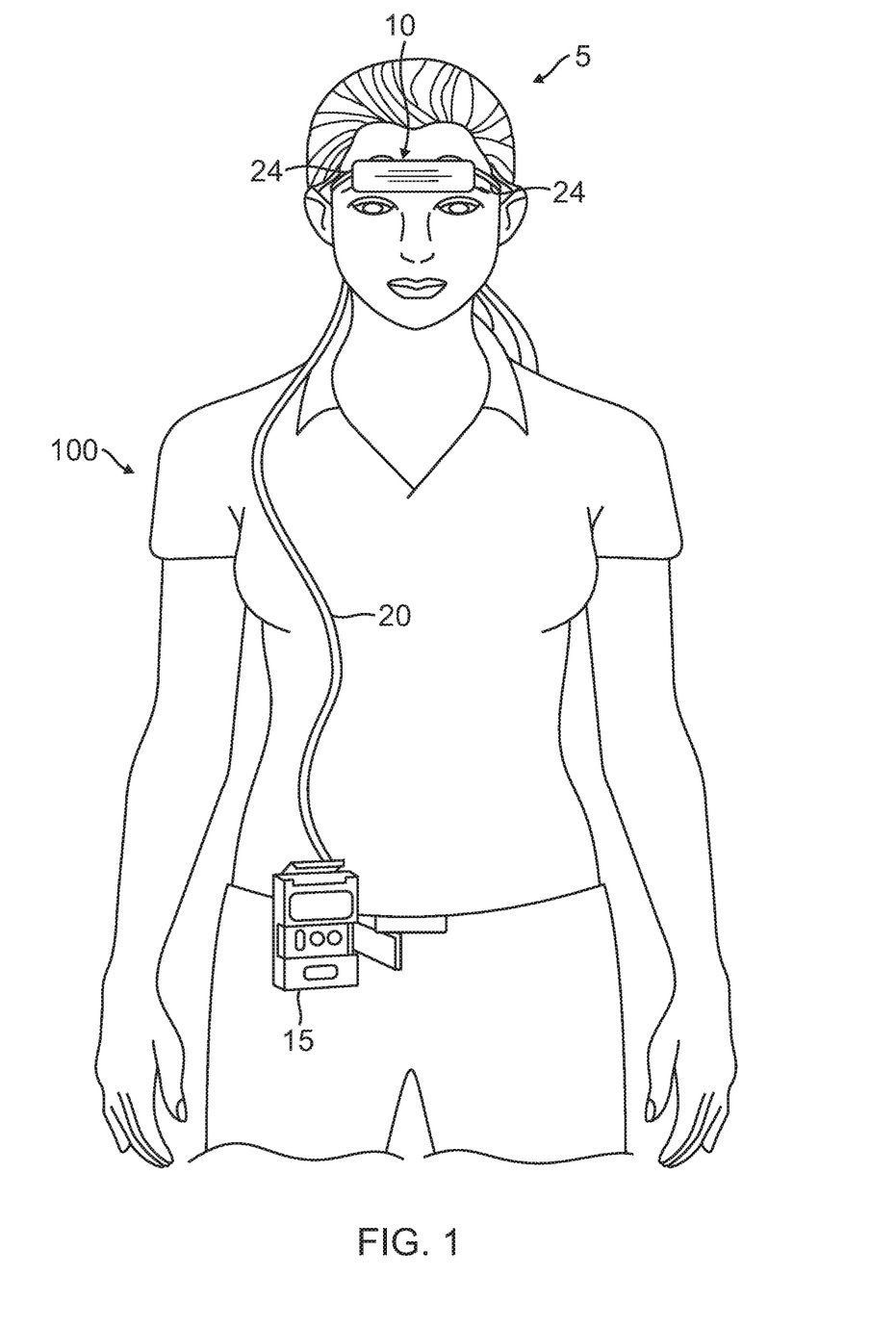
FIG. 1 illustrates a subject wearing a cutaneous electrode for TNS therapy.

To provide efficacious trigeminal neurostimulation therapy without the need for daily medical facility visits, a cutaneous electrode assembly 10 as seen in TNS system 100 of FIG. 1 supports electrodes (not illustrated) such that if a patient medially centers electrode assembly 10 across their forehead, the contained electrodes are then positioned over the supraorbital and/or supratrochlear trunks. To ensure the maximum coverage or stimulation of each supraorbital and supratrochlear nerve trunk, the patent may be instructed to align an inferior edge of electrode assembly just above their orbital arches. If electrode assembly 10 has electrodes configured for bilateral stimulation of the trigeminal, one or more electrodes will thus be on located above each orbit and over the supraorbital notches such that a pulse transmitted between the electrical contacts for each orbit will conducts across the supraorbital and supratrochlear nerve fibers as they arise from their respective orbits. Moreover, these nerve branches are relatively shallow with regard to the forehead skin surface and thus readily stimulated by electrode assembly 10.

A patient can easily apply electrode assembly 10 in the correct position by centering it across the forehead median. Although electrode assembly 10 has conductive gel so as to adhere to the forehead, a retainer device 24 may also be used to help secure electrode assembly 10. A pulse generator 15 drives electrode assembly 10 through a cable 20. It is important that a patient be able to correctly position a TNS electrode so that the appropriate nerves are stimulated without the risks of current penetration to the brain. Because a patient can readily position electrode assembly 10 medially on their forehead using a landmark such as their nasal midline, the patient needs no knowledge of anatomy in that regard yet they are positioning the electrode in an advantageous location for TNS therapy. Studies have shown that TNS carried out in this fashion are significantly more efficacious than the use of conventional VNS. Yet TNS is far less invasive, has much fewer risks, and considerably lower cost than VNS.

Although TNS is thus an attractive alternative to VNS, problems remain with regard to it use. For example, it is conventional in the cutaneous electrode arts to use a conductive gel to adhere an electrode to the skin. The gel is quite sticky and serves as both an adhesive and an electrical conductor. It is thus conventional to apply EEG and EKG electrodes using conductive gel. Similarly, conductive gel is used to apply TENS (transcutaneous electrical nerve stimulation) electrodes. But such applications are relatively temporary. In contrast, the electrical stimulation from TNS may need to be applied for hours at a time such as while sleeping or even 24 hours a day. The forehead is a problematic environment for such long-term adhesion as the forehead skin is generally quite oily. Moreover, the excessive oil tends to make the forehead more prone to contaminates such as dust or dirt. An electrode applied with conductive gel to the forehead will thus tend to come off during such relatively-long periods of time. This is problematic as the electrode can only provide therapy while it is attached to the patient. Moreover, the peeling off of the electrode can induce arcing from the electrode to the patient. Accordingly, there is a need in the art for improved TNS electrodes.

SUMMARY

A windowed electrode assembly includes a foam layer having windows. Each window receives a corresponding gel pad that is sized such that it is contained by the window's sidewalls. The windowed electrode assembly includes a foam backing layer that forms a back wall for the windows such that each gel pad is encased by the window's sidewalls and back wall.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION

Reference will now be made in detail to one or more embodiments of the invention. While the invention will be described with respect to these embodiments, it should be understood that the invention is not limited to any particular embodiment. On the contrary, the invention includes alternatives, modifications, and equivalents as may come within the spirit and scope of the appended claims. Furthermore, in the following description, numerous specific details are set forth to provide a thorough understanding of the invention. The invention may be practiced without some or all of these specific details. In other instances, well-known structures and principles of operation have not been described in detail to avoid obscuring the invention.

As used herein, an "electrode assembly" refers to a generally planar framework that supports one of more electrodes for cutaneous stimulation of the ophthalmic nerves on patient's forehead. As further used herein, an "ophthalmic nerve pair" refers to the supraorbital nerve and supratrochlear nerve that arise from the same supraorbital arch or orbit. It is thus convenient for each electrode in an electrode assembly to have a size sufficient to excite both nerves in a given ophthalmic nerve pair. As will be explained further below, the novel electrode assemblies disclosed herein may be denoted as "windowed" electrode assemblies in that a windowed electrode assembly encases each electrode in a window or cavity. In other words, a windowed electrode assembly has a skin-facing planar surface that is configured to adhere to a patient's forehead using medical-grade adhesive. The windows are defined with regard to this planar surface and backed by an opposing outward-facing surface of the windowed electrode assembly. Each window encases a corresponding electrode that comprises conductive gel. This is quite advantageous in that adhesive surface of the windowed electrode assembly keep the windowed electrode assembly removably fastened to a patient's forehead without the possibility of the conductive gel oozing out from the applied windowed electrode assembly and leading to patient discomfort and reduction of therapeutic efficacy. Each conductive gel electrode is then encased in that it is surrounded by the adhesive skin-facing surface of the windowed electrode assembly, the sidewalls of the corresponding window, and a back wall of the corresponding window as discussed further herein.

Figures 2A, 2B:
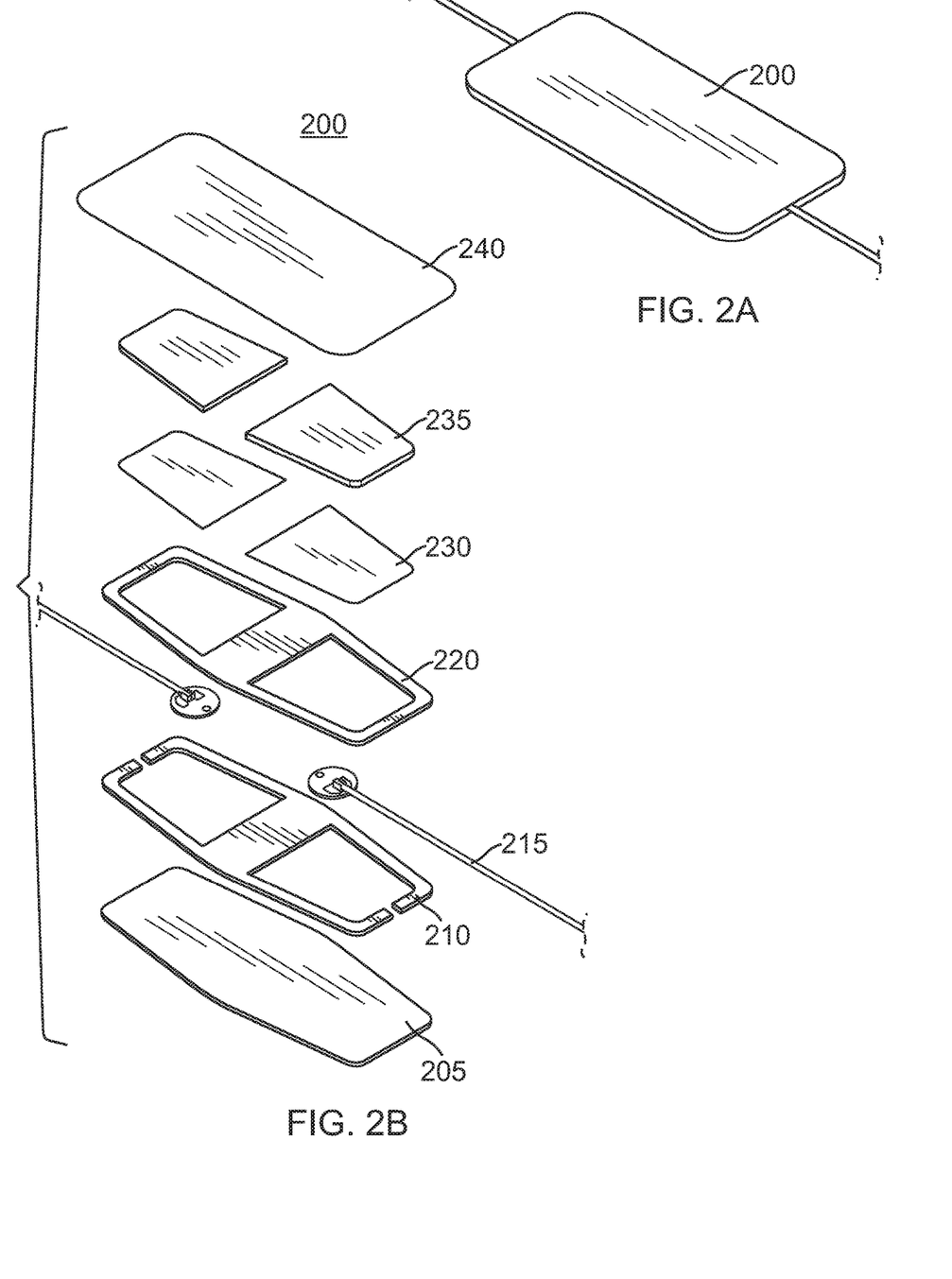
FIG. 2A is a perspective view of an example cutaneous electrode assembly.
FIG. 2B is an exploded view of the electrode assembly of FIG. 2.

Each windowed electrode assembly has a longitudinal extent sufficient to extend from the lateral portion of one supraorbital arch on a patient's forehead to a lateral portion of the opposing supraorbital arch. Given this longitudinal extent, if a patient medially centers the electrode assembly above their supraorbital arches with regard to their nasal midline, the electrode assembly will extend substantially across each supraorbital arch. As will be explained further below, each lateral end of the longitudinally-extending windowed electrode assembly includes a window positioned such that when the patient centers the windowed electrode assembly as discussed above on their forehead, each ophthalmic nerve pair is covered by a corresponding window in the windowed electrode assembly. Some example embodiments will now be discussed in more detail. Referring now to FIG. 2A, a windowed electrode assembly 200 is shown that addresses the problems discussed above with regard to conventional electrode design for TNS therapy. FIG. 2B is an exploded view of windowed electrode assembly 200. To adhere windowed electrode assembly 200 to the forehead, the user first pulls off a flexible plastic release liner 240. Prior to use, release liner 240 protects a pair of gel pads 235, which are laterally positioned in an opposing fashion with regard to the longitudinal center of windowed electrode assembly 200 in corresponding windows of a skin-facing foam layer 220. In this fashion, when windowed electrode assembly 200 is centered on the forehead analogously as shown in FIG. 1 (more generally, when the longitudinal center of electrode assembly 200 is aligned with the nasal midline/forehead midline), each electrode/gel pad 235 cover the trunks of the supraorbital and supratrochlear nerves in a corresponding ophthalmic nerve pair as they ascend from the orbit superiorly towards the hairline. The excitation from windowed electrode assembly 200 is thus bilateral in that one gel pad 235 acts as a cathode (or anode) and a remaining gel pad 235 acts as the corresponding anode (or cathode). If the excitation is AC, then the cathode and anode roles for gel pads 235 are periodically reversed depending upon the current phase for the AC excitation. As an electrical pulse is generated from one pad 235 to the other, the pulse will conduct across the supraorbital and supratrochlear nerve fibers to stimulate them. The resulting stimulation is then conducted down the afferent branches of the nerves to the brain. Advantageously, windowed electrode assembly 200 locates pads 235 when centered on the forehead such that virtually no electrical current actually enters the brain. For example, a charge density of less than 0.001 $\mu C/cm^2$ to no more than 0.1 $\mu C/cm^2$ of current penetrates to the cerebral cortex. Instead of inducing current in the brain, the wave of pulses applied transcutaneously to the forehead induces neuronal signaling events that alleviate neurological disorders such as epilepsy. Moreover, other conditions also respond to TNS therapy such as migraines, acute brain injury, and chronic headache.

In an alternative embodiment, each window in windowed electrode assembly 200 would be replaced by a inferiorly-to-superiorly oriented pair of windows such that the excitation from the corresponding pads/electrodes may be performed in an afferent direction with regard to a given nerve trunk. Alternatively, each window may be replaced by a medially-to-laterally oriented pair of windows such that an ophthalmic nerve pair may be unilaterally stimulated. Regardless of the window geometry, gel pads 235 may be formed from a suitable conductive gel such as a hydrogel and are received in corresponding windows in skin-facing foam layer 220. In other words, gel pads 235 lies within corresponding windows in skin-facing foam layer 220. The sidewalls for each window thus comprise the edges of window in skin-facing foam layer 220. Prior to removal of release layer 240, gel pads 235 are sandwiched between release layer 240, the sidewalls for corresponding window, and a back wall for the corresponding window as formed by a conductive film patch 230. An additional foam layer 210 also includes windows for gel pads 235. Foam layers 210 and 220 are aligned such that their windows align. Each gel pad 235 is thus contained by the sidewalls of the corresponding windows in foam layers 210 and 220 and a back wall formed by the corresponding conductive film patch 230. A skin-facing surface of foam layer 220 that faces release liner 240 is coated with a medical grade adhesive such that foam layer 220 acts as a medical grade tape when applied to the skin of the forehead. Each window in additional foam layer 210 receives a wire assembly 215 that is located anteriorly to the corresponding conductive film patch 230. Each wire assembly 215 comprises a conductive lead driving a metallic disk (electrical contact) so that, during use, a pulse generator coupled to the wire assemblies 215 can drive electrical pulses through conductive film patches 230 and gel pads 235 to stimulate the desired nerve branches. A base foam layer 205 provides a backing to the remaining electrode components to support each window back wall formed by the corresponding conductive patch 235 and wire assembly 215.

Figure 3A:
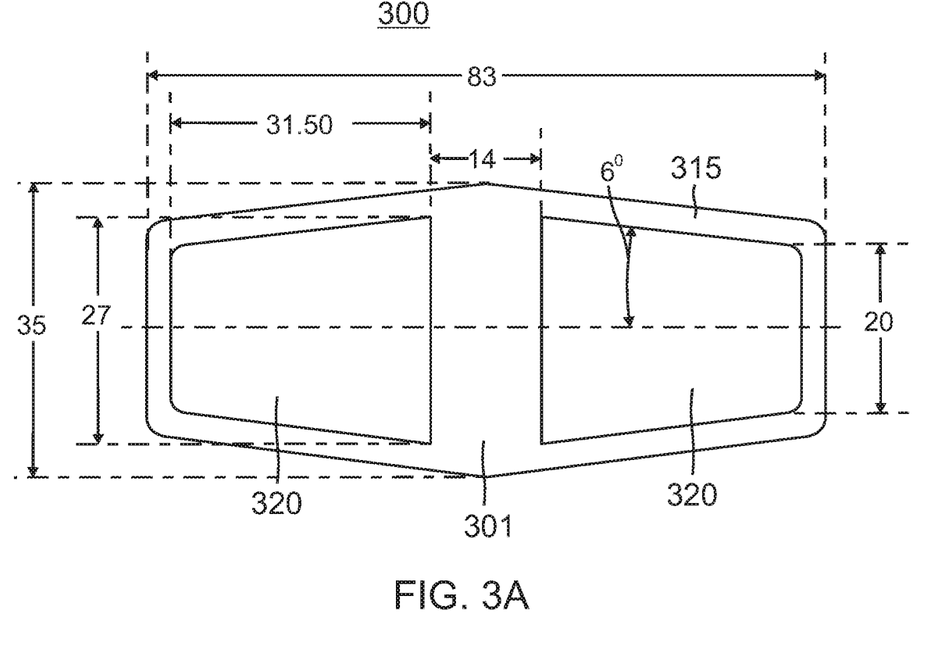
FIG. 3A is a plan view of an electrode assembly with alignment features.
Figure 3B:
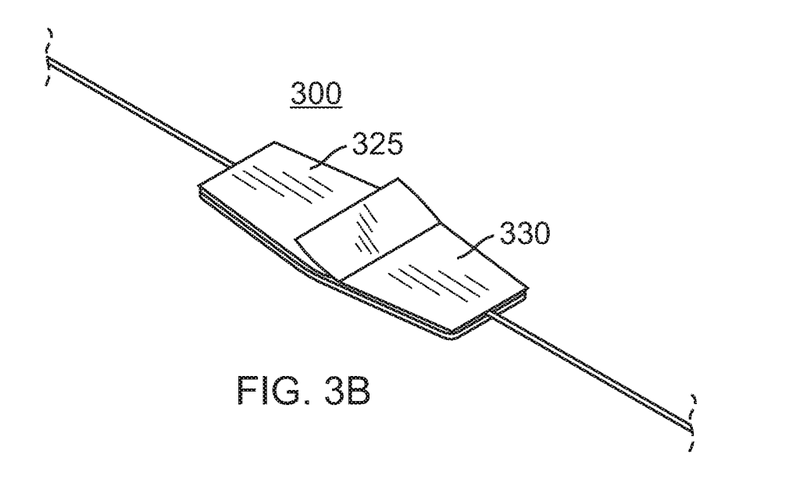
FIG. 3B is a perspective view of the electrode assembly of FIG. 3A.
Figure 3C:
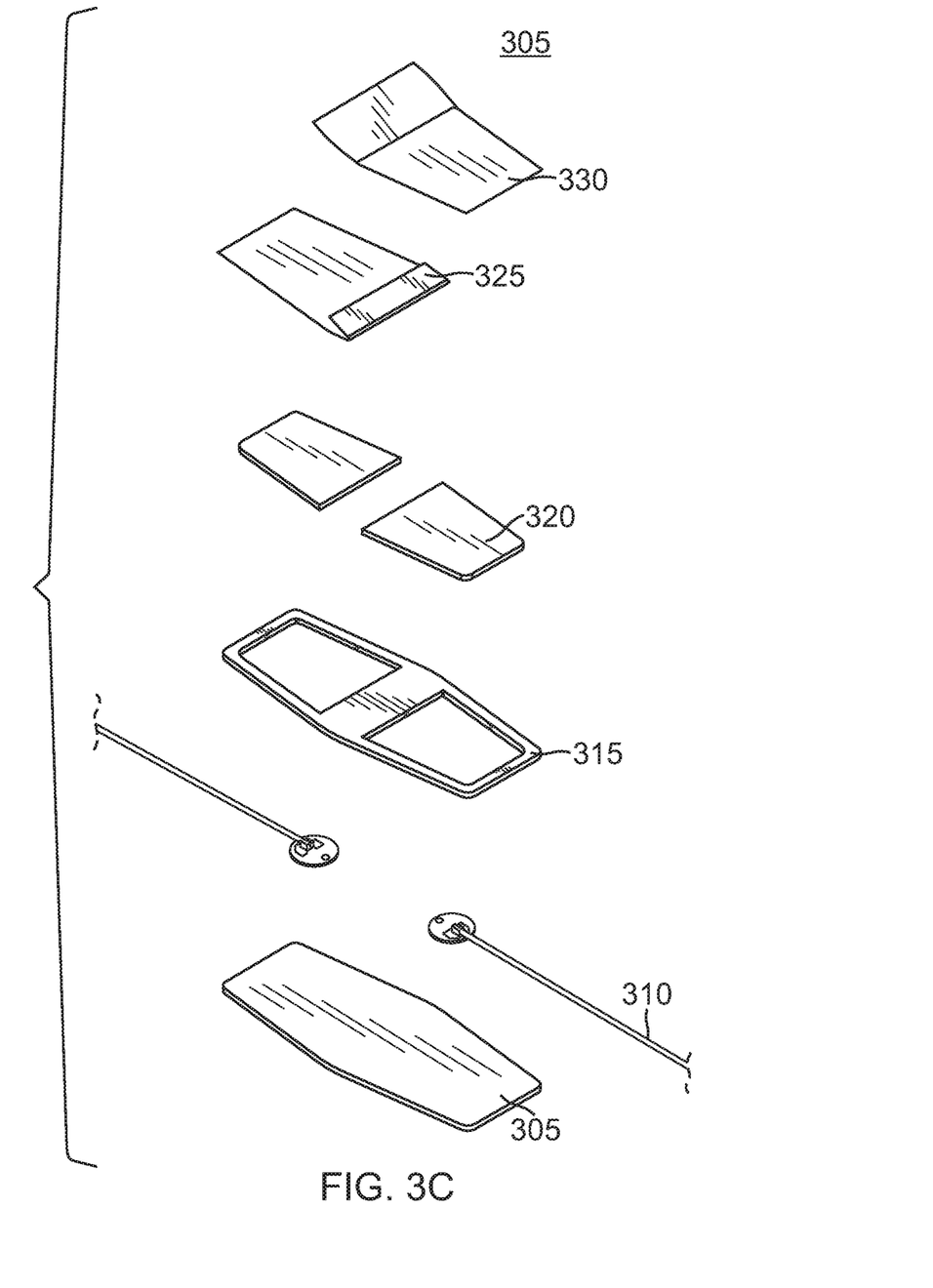
FIG. 3C is an exploded view of the electrode assembly of FIG. 3A.

An alternative embodiment for a windowed electrode assembly 300 is illustrated in FIGS. 3A, 3B, and 3C in which the flexible release liner is replaced by waxed paper flaps 330 and 325. FIG. 3A is a plan view of a skin-facing surface of windowed electrode assembly 300 after removal of flaps 330 and 325 whereas FIG. 3B is a perspective view of windowed electrode assembly prior to removal of the flaps. Flaps 3230 and 335 function in the familiar "band aid" fashion such that each flap includes a projecting end that a user may readily pull on to release the corresponding flap from windowed electrode assembly 300. Rather than use two foam layers having corresponding windows, each window in windowed electrode assembly 300 is formed in a single foam layer 315. The sidewalls for each window in foam layer 315 thus encase a corresponding gel pad 320. Gel pads 320 directly contact corresponding wire assemblies 310 although a conductive patch similar to that described for windowed electrode assembly 200 may also be used. Because the conductive patches are absent in windowed electrode assembly 300, a foam backing layer 305 not only supports the remaining components but also forms a back wall for each window. A medical-grade adhesive on the skin-facing surface of foam layer 315 keeps flaps 325 and 330 adhered until they are removed and the skin-facing surface of foam layer 315 then applied to the forehead.

To aid in the alignment of windowed electrode assembly 300 on the forehead, a suitable anatomical landmark is the nasal midline. Windowed electrode assembly 300 is aligned on the forehead so that its midline aligns with the nasal midline. To assist such an alignment, a midline alignment feature may be provided. For example, windowed electrode assembly 300 may have an elongated hexagonal shape such that each longitudinal side forms a convex angle at the electrode midline. A user may thus readily align features 301 with their nasal midline when applying electrode assembly 300 to their forehead.

The dimensions of a windowed electrode assembly such as assemblies 200 and 300 depend upon the age of the patient. In a typical adult, the foramen (or notch) for the supratrochlear nerve is approximately 2.1 to 2.6 cm from the nasal midline with regard to the corresponding orbit. In contrast, the foramen (or notch) for the supraorbital nerve is located more laterally from the nasal midline: e.g., approximately 3.2 cm from the nasal midline in adults. Given this anatomy, a convenient longitudinal extent for a windowed electrode assembly such as assembly 300 is 8.3 centimeters whereas its height at the midline is 3.5 cm. The medial edge of each window for the corresponding gel pad 320 is 7 mm from the midline such that gel pads 320 are separated by 14 mm. Given the chevron shaping resulting from alignment features 301, each pad 320 narrows by 12 degrees from a medial edge of a 27 mm to a lateral edge of 20 mm over a width of 31.5 mm. The lateral edge of each pad 320 is thus 38.5 mm from the nasal midline. Such a pad spacing assures that each pad 320 is positioned to stimulate both the trunk of the supraorbital nerve and the trunk of the supraorbital nerve in an ophthalmic nerve pair for the vast bulk of the adult population. But some adults will require even a greater pad width such as 34 mm to assure that the supraorbital nerves receive adequate stimulation.

Figure 4:
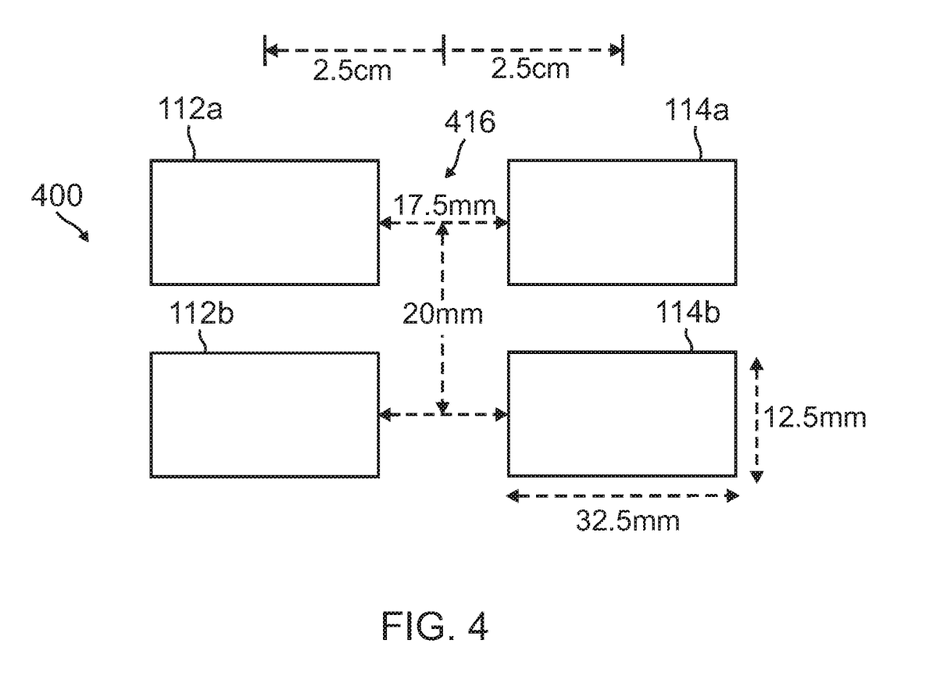
FIG. 4 is a plan view of a unilateral windowed electrode assembly window layout.

The bilateral stimulation from using at least two gel pads such as gel pads 235 or 320 is advantageous in that the function of brain structures may vary in the left and right hemispheres. Moreover, it is believed that bilateral stimulation may lead to synergistic effects that increase therapeutic efficacy. However, the present disclosure also includes embodiments in which the pads are positioned for unilateral nerve stimulation as discussed earlier. For example, FIG. 4 illustrates a window layout for a unilateral windowed electrode assembly 400. A first pair of gel pads 112a and 112b are located for placement above the supraorbital ridge at one side of the forehead. Similarly, a second pair of gel pads 114a and 114b are located for placement above the supraorbital ridge on an opposing side of the forehead of a patient. The first and second gel pad pairs are insulated from other by an insulative connection region 416. Each gel pad 112a, 112b, 114a, and 114b has a width equal to or greater than the expected separation between a supraorbital nerve and the adjacent supratrochlear nerve in an ophthalmic nerve pair. The electrode assembly 400 may be configured to stimulate both the right and left ophthalmic nerve pairs either simultaneously or asynchronously. The insulative connection region 416 serves to assist a patient in lining up the electrode assembly 400 with the midline of the nose to ensure proper placement of the electrode assembly 400 over both ophthalmic nerve pairs. As discussed earlier, the supratrochlear foramen (or notch) will typically be located about 2.1 to 2.6 cm from the nasal midline of an adult patient. Similarly, the supraorbital foramen (or notch) will typically be located about 3.2 cm from the nasal midline of an adult patient. The nerve fibers will tend to rise in a parallel fashion from notches. In other words, if an electrode has a width sufficient to overlay the foramina for an ophthalmic nerve pair, that same contact would also overlay the corresponding ophthalmic nerve pair fibers if moved further up the forehead toward the hairline. Each electrode should thus have a width and a positioning such that both nerves in the corresponding ophthalmic nerve pair are stimulated. By aligning region 416 with the nasal midline, a patient may readily position windowed electrode assembly 400 on the forehead without knowledge of the location of the ophthalmic nerve pairs or their foramina, thereby reducing the possibility of inadequate stimulation due to errors in positioning of the electrodes.

In one embodiment, the mid-point of each of the gel pads is approximately 2.5 cm (in other embodiments, such a mid-point may range from 1.5 cm to 3.5 cm) from the nasal midline. The electrode size and the inter-electrode distance may vary for children and adults, males and females based on anatomical differences. Each electrode is approximately 32.5 mm in width by 12.5 mm in height and the distance between, for example, the upper pair of electrodes 112a and 114a is 17.5 mm. The separation between each electrode pair (e.g. between upper electrode 112a and the lower electrode 112b is 20 mm. It is simpler, however, to direct the current neither in an afferent nor in an efferent fashion but instead orthogonally across the fibers using just a single pair of electrodes as discussed with regard to electrode assemblies 200 and 300.

Referring again to FIG. 1, pulse generator 15 is portable and attached to the belt of a patient 20. However, either a portable or non-portable pulse generator may be used. In alternative embodiments, a windowed electrode assembly 100 may be integrated with a pulse generator. Regardless of whether a single pair of electrodes are used to stimulate both ophthalmic nerve pairs or whether each ophthalmic nerve pair is stimulated by its own pair(s) of electrodes, the current from the pulse generator may be pulsed at a stimulus frequency between about 20 Hz and about 300 Hz, at a pulse duration between 50 microseconds (μsec) and 250 μsec, at an output current density of less than 25 mA/cm2 and an output charge density of less than 10μ Coulomb/cm2 at the cerebral cortex for at least one-half to one hour per day. The pulsing may be performed in a duty cycle of 30 seconds of pulsing following by 30 seconds of rest.

In various embodiments, the stimulation is delivered at a specific pulse width or range of pulse widths (or pulse duration). The stimulation can be set to deliver pulse widths in any range within a lower limit of about 10 microseconds and an upper limit of about 3 seconds. In various embodiments, the stimulation can be set to deliver pulse widths in the range greater than and/or less than one or more of 50 μsec, 60 μsec, 70 μsec, 80 μsec, 90 μsec, 100 μsec, 125 μsec, 150 μsec, 175 μsec, 200 μsec, 225 μsec, 250 μsec, up to 500 μsec. Those of skill in the art will recognized that one or more of the above times can be used as a border of a range of pulse widths.

It will be appreciated that the techniques and concepts discussed herein are not limited to the specific disclosed embodiments. The appended claims encompass all such changes and modifications as fall within the true spirit and scope of this invention.

I claim:

1. A method, comprising:
    placing a first gel pad provided in a first window of a cutaneous windowed electrode assembly over an ophthalmic nerve pair with regard to one orbit on a patient's forehead;
    placing a second gel pad provided in a second window of the cutaneous windowed electrode assembly over the ophthalmic nerve pair for a remaining orbit on the patient's forehead; and
    driving current between the first and the second gel pads to bilaterally stimulate the ophthalmic nerve pair to treat a disorder for the patient.

2. The method of claim 1, further comprising removing a pair of flaps from the cutaneous windowed electrode assembly prior to its application to expose an adhesive surface for the cutaneous windowed electrode assembly, and wherein the adhesive surface is adhered to the patient's forehead.

3. The method of claim 1, wherein the cutaneous windowed electrode assembly includes at least one alignment feature, the method further comprising aligning the at least one alignment feature with a nasal midline of the patient when placing the first and the second gel pads on the patient's forehead.

4. The method of claim 3, wherein the at least one alignment feature has an elongated hexagonal shape forming a convex angle configured to accommodate the nasal midline of the patient.

5. The method of claim 3, wherein the at least one alignment features comprises a planar foam layer and a planar foam backing aligned with the planar loam layer each having chevron shape configured to accommodate the nasal midline of the patient.

6. The method of claim 1, wherein the mid-point of each of the first and the second gel pads is located between 1.5 cm and 3.5 cm from a longitudinal center of the windowed electrode assembly.

7. The method of claim 1, wherein driving the current between the first and the second gel pads comprises driving the current from a pulse generator integrated with the cutaneous windowed electrode assembly.

8. The method of claim 1, wherein driving the current between the first and the second gel pads comprises driving the current from a non-integrated pulse generator.

9. The method of claim 1, wherein the current is provided to the first and the second gel pads via electrical contacts coupled to conductive film patches.

10. The method claim 1, wherein the current stimulates the ophthalmic nerve pair in an afferent direction.

11. The method of claim 1, wherein the current stimulates the ophthalmic nerve pair in an efferent direction.

12. The method of claim 1, wherein each of the first and the second window extends laterally to cover both a supraorbital nerve trunk and a supratrochlear nerve trunk in the ophthalmic nerve pair.

13. The method of claim 1, wherein a size or a dimension of the cutaneous windowed electrode assembly is adjusted or selected based on an age of the patient.

14. A method, comprising:
    placing a first pair of gel pads of a cutaneous windowed electrode assembly over an ophthalmic nerve pair with regard to one orbit on a patient's forehead;

placing a second pair of gel pads of the cutaneous windowed electrode assembly over the ophthalmic nerve pair for a remaining orbit on the patient's forehead; and driving current in each of the first and the second pairs of gel pads to stimulate the ophthalmic nerve pair to treat a disorder for the patient.

15. The method of claim 14, further comprising removing a pair of flaps from the cutaneous windowed electrode assembly prior to its application to expose an adhesive surface for the cutaneous windowed electrode assembly, and wherein the adhesive surface is adhered to the patient's forehead.

16. The method of claim 14, wherein the cutaneous windowed electrode assembly includes at least one alignment feature, the method further comprising aligning the at least one alignment feature with a nasal midline of the patient when placing the first and the second pairs of gel pads on the patient's forehead.

17. The method of claim 16, wherein the at least one alignment features comprises a planar foam layer and a planar foam backing aligned with the planar loam layer each having chevron shape configured to accommodate the nasal midline of the patient.

18. The method of claim 14, wherein the first and the second pairs of gel pads stimulate the ophthalmic nerve pair simultaneously.

19. The method of claim 14, wherein the first and the second pairs of gel pads stimulate the ophthalmic nerve pair asynchronously.

20. The method of claim 14, wherein driving the current in each of the first and the second pairs of gel pads comprises driving the current from a pulse generator integrated with the cutaneous windowed electrode assembly.

* * * * *